United States Patent
Marks et al.

(10) Patent No.: US 6,235,918 B1
(45) Date of Patent: May 22, 2001

(54) SUPPORTED ORGANOMETALLIC CATALYSTS FOR HYDROGENATION AND OLEFIN POLYMERIZATION

(75) Inventors: Tobin J. Marks; Hongsang Ahn, both of Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/364,216

(22) Filed: Jul. 29, 1999

Related U.S. Application Data

(60) Provisional application No. 60/094,495, filed on Jul. 29, 1998.

(51) Int. Cl.[7] .............. C07F 17/00; C07F 7/00; B01J 31/00
(52) U.S. Cl. .............. 556/53; 556/43; 556/70; 556/87; 556/170; 556/465; 556/52; 502/120; 502/122; 526/160; 526/943
(58) Field of Search ............... 556/53, 87, 170, 556/465, 43, 70, 52; 502/120, 122; 526/160, 943

(56) References Cited

PUBLICATIONS

Xuemin Song and Abdelhamid Sayari. Sulfated Zirconia–Based Strong–Acid Catalysts: Recent Progress. (1996) Catalysis Review—Science Engineering, vol. 39(3), p. 329–412.

V. Bolis, G. Magnacca, G. Cerrato, and C. Morterra. Microcalorimetric Characterization of Structural and Chemical Heterogeneity of Superacid $SO_4/ZrO_2$ Systems. (1997) Langmuir, vol. 12, p. 888–894.

H. Armendariz, C. Sanchez Sierra, F. Figueras, B.Coq, C. Mirodatos, F. Lefebvre, and D. Tichit. Hydrogen Exchange between Sulfated Zirconias and per Deutero–Benzene as Characterization of Surface Acidity. (1997) Journal of Catalysis, vol. 171, p. 85–92.

A. Clearfield, G.P.D. Serrette, A.H. Khazi–Syed. Nature of hydrous zirconia and sulfated hydrous zirconia. (1994) Catalysis Today, vol. 20, p. 295–312.

David A. Ward and Edward I. Ko. One–Step Synthesis and Characterization of Zirconia–Sulfate Aerogels as Solid Superacids. (1994) Journal of Catalysis, vol. 150, p. 18–33.

Patrice Batamack, Imre Bucsi, Arpad Molnar and George A. Ohah. Electrophilic chlorination of methane over superacidic sulfated zirconia. (1994) Catalysis Letters, vol. 25, p. 11–19.

A.S. Zarkalis, C.Y. Hsu and B.C. Gates. Solid superacid catalysis: kinetics of butane isomerization catalyzed by a sulfated oxide containing iron, manganese, and zirconium. (1994) Catalysis Letters, vol. 29, p. 235–239.

Dan Farcasiu, Jing Qi Li, Andreas Kogelbauer. The mechanism of conversion of hydrocarbons on sulfated metal oxides. Part IV. Kinetics of the reactions of methylcyclopentane on sulfated zirconia. (1997) Journal of Molecular Catalysis A. Chemical, vol. 124, pp. 67–78.

E. Escalona Platero and M. Peñarroya Mentruit. IR Characterization of sulfated zirconia derived from zirconium sulfate. (1995) Catalysis Letters, vol. 30, pp. 31–39.

Jean Sommer, David Habermacher, Mohammed Hachoumy, Roland Jost, Antoine Reynaud. The H/D exchange reaction occurring at low temperature between small alkanes and $D_2O$ exchanged solid acids. III. The role of alkenes and carbenium ions as reaction intermediates. (1996) Applied Catalysis A: General, vol. 146, p. 193–205.

V. Adeeva, J.W. de Haan, J. Jänchen, G.D. Lei, V. Schünemann, L.J.M. van de Ven, W.M.H. Sachtler, and R.A. van Santen. Acid Sites in Sulfated and Metal–Promoted Zirconium Dioxide Catalysts. (1995) Journal of Catalysis, vol. 151, p. 364–372.

*Primary Examiner*—Porfirio Nazario-Gonzalez
(74) *Attorney, Agent, or Firm*—Welsh & Katz, Ltd.

(57) ABSTRACT

Novel heterogeneous catalysts for the which hydrogenation of olefins and arenes with high conversion rates under ambient conditions and the polymerization of olefins have been developed. The catalysts are synthesized from Ziegler-type precatalysts by supporting them on sulfate-modified zirconia.

1 Claim, 1 Drawing Sheet

SUPPORTED ORGANOMETALLIC CATALYSTS FOR HYDROGENATION AND OLEFIN POLYMERIZATION

Figures 1A, 1B:
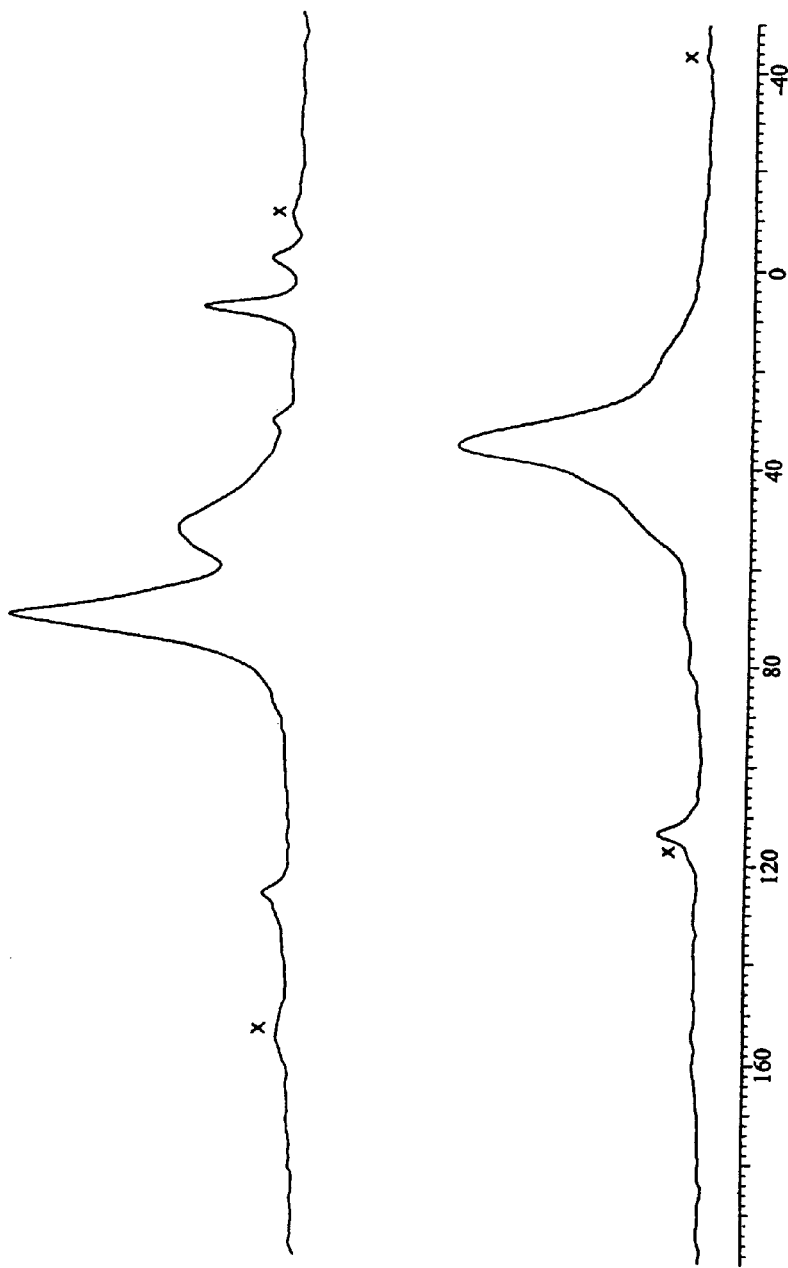

This Appln claims the benefit of Provisional No. 60/094,495 filed Jul. 29, 1998.

This invention was made with Government support under Contract No. DE- FG02-86ER13511 awarded by the Department of Energy. The Government has certain rights in this invention.

BACKGROUND OF THE INVENTION

This invention relates to compositions of matter useful as a catalyst system, to a method for preparing these catalyst systems and to methods for polymerization and hydrogenation utilizing the catalyst system.

The use of Ziegler-Natta type catalysts in the polymerization of olefins is well known in the prior art. In general, such systems include a Group 4 metal compound with a metal or metalloid alkyl cocatalyst, such as aluminum alkyl cocatalyst for homogenous systems or metal oxide/organo-Lewis acid activated metal-oxide for heterogeneous systems. More broadly, it may be said to include a mixture of a Group 1,2 or 13 metal alkyl and a transition metal complex from the Group 4 metals, particularly titanium, zirconium, or hafnium with homogeneous/heterogeneous cocatalysts.

Many current Ziegler-Natta processes are designed for gas phase or slurry reaction in solution, and heterogenization of homogeneous Ziegler-type catalysts to optimize polymerization activity and polymer producing properties such as stereoregularity, molecular weight, thermal/rheological characteristics, bulky and polar comonomer incorporation and microstructure are of great advantage. Studies of homogenous Ziegler-type catalysts have shown that highly electrophilic cationic species (e.g., A) can be produced using organo-Lewis acidic (alkide/hydride abstraction) and Brønsted acidic (M-alkyl/H proteolysis) cocatalysts. In contrast, our overall understanding and application of analogous supported organometallic catalysts has been exclusively confined to Lewis acid surfaces or to organo-Lewis acid activated surfaces, since adsorption of metallocenes on conventional Brønsted acid surfaces typically results in a catalytically inert μ-oxo species (B) via protonolysis.

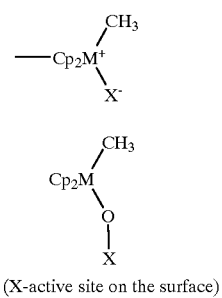

(X-active site on the surface)

A design for a weakly coordinating anionic surface, derived from a very strongly Brønsted acidic surface is an essential key to developing new heterogeneous Ziegler-Natta processes. Recently, sulfated zirconia and related solid acids have received considerable attention because of their claimed "superacidity" i.e., stronger acidity than 100% $H_2SO_4$ (Hammett acid value $H_o=-12$), a property which was suggested by paraffin isomerization at room temperature. These strongly acidic sulfate group activated surfaces can be superior candidates for supports rather than MAO (methylalumoxane) or organo-Lewis acid activated ones.

SUMMARY OF THE INVENTION

Accordingly, it is an object of the subject invention to prepare and utilize a new class of olefin and arene hydrogenation and α-olefin polymerization catalytic system.

A further object of the subject invention is a catalytic system which permits increased hydrogenation activity and polymerization activity.

Another object of the subject invention is a Ziegler-Natta type catalytic system which involves adsorbing the catalysts on sulfate-modified zirconia or related materials.

These and other objects are attained by the subject invention whereby in one embodiment, there is a new method of synthesis of highly active cationic metallocene hydrogenation and polymerization catalysts formed via protonolytic chemisorption by sulfated zirconia, including the novel catalytic system itself.

The catalyst systems of the subject invention are synthesized through adsorption of Ziegler-type catalysts on sulfate-modified zirconia or related materials. Ziegler-type catalysts are slurried with sulfate-modified zirconia in hydrocarbon solvents under anaerobic conditions, and thereby irreversibly adsorbed on the surface. Hydrogenation and polymerization catalyst systems are obtained from the dried, impregnated substrates.

More specifically, the subject invention involves methods for catalytic arene/olefin hydrogenation as well as olefin polymerization catalysis by organo-group 4 and 5 molecules such as $R_xMR^1_y$, where R, $R^1$ is a cyclopentadienyl ligand, an alkyl (C≦20), an alkenyl (C≦20), or an aryl group (C≦20)

M is Zr, Ti, Hf, V, Nb, Ta, Lanthanide, Al, Si, Ge, Sn, Pb, As, Sb, or B;

X is 0 to 3

Y is 0 to 3

The above compound is adsorbed on sulfate-modified zirconia (ZR), zirconia/tungsten oxide (ZRW), highly Brønsted acidic sulfated zirconia (ZRSX, where x indicates the activation temperature), sulfated zirconia on coated silica, and other sulfated metal oxides based on Ti, Hf., Si, Sn, Fe, or Al.

CONCISE DESCRIPTION OF THE DRAWINGS

FIGS. 1(a) and 1(b) are $^{13}C$ NMR spectra establishing the molecular structures of the catalytic complexes of the subject invention.

DETAILED DESCRIPTION OF THE INVENTION

Materials and Methods. All procedures were performed in Schlenk-type glassware interfaced to a high-vacuum ($10^{-5}$–$10^{-6}$ Torr) line or a nitrogen-filled Vacuum Atmosphere glovebox (0.5–1 ppm of $O_2$). Argon (Matheson), hydrogen (Matheson), ethylene (Matheson), and propylene (Matheson) were purified by passage through MnO/vermiculite and Davison 4A molecular sieves columns. Oxygen (Matheson) was dried by passage through Drierite (Hammond Co.). All solvents, 1-hexene (Aldrich), and arenes (Aldrich) were distilled from Na/K alloy. The organometallic complexes $Ti(CH_2CMe_3)_4$, $CpTi(CH_3)_3$, $Cp^*Ti(CH_3)_3$, $Cp_2Zr(CH_3)_2$, $Cp^*_2Hf(CH_3)_2$, $Cp^*Zr(CH_3)_3$, CGCZr(CH$_3$)$_2$, Zr(CH$_2$SiMe$_3$)$_4$ Ta(CH$_2$CMe$_3$)$_3$(=CHCMe$_3$), Cp*Ta(CH$_2$Ph)$_2$(=CHPh), Cp*Ta(CH$_3$)$_3$ were prepared by the literature procedures. Cp$_2$Zr($^{13}$CH$_3$)$_2$, CP*Zr($^{13}$CH$_3$)$_3$, CpTi($^{13}$CH$_3$)$_3$, and Cp*$_2$Th($^{13}$CH$_3$)$_2$ were synthesized from $^{13}$CH$_3$I (99% $^{13}$C, Cambridge Isotopes) using analogous methods. Sulfated zirconia was prepared by thermal decomposition of Zr(SO$_4$)$_2$·4H$_2$O (3.5 g, Aldrich, 99%) at 730° C. for 5 hr in flowing O$_2$ (100 mL/min). Then the samples were activated at 400° C. under high-vacuum (5×10$^{-6}$Torr). Zirconia (ZR) and tungsten-oxide/zirconia (ZRW) were synthesized as follows: 1) Aqueous ammonium was added to an aqueous solution of ZrOCl$_2$ (Aldrich) until pH=~10. A resulting precipitate was filtered, dried under air at 100° C. for 12 h, and then calcined under flowing dry O$_2$ (100 mL/min) at 500° C. for 10 h, yielding zirconia (ZR). 2) Zr(OH)$_3$ obtained by hydrolysis of ZrOCl$_2$ (Aldrich) was mixed with an aqueous solution of (NH$_4$)$_6$W$_{12}$O$_{39}$5H$_2$O (Aldrich), dried under air at 120° C. for 12 h, and calcined under flowing dry O$_2$ (100 ml/min) at 200° C. for 2 h; dry O$_2$, 800° C.,3 h; high-vacuum, 900° C., 0.5 h, yielding tungsten-oxide/ zirconia (ZRW). ZRS 300 and ZRS 400 may be prepared by thermally decomposing Zr(SO$_4$)$_2$·4H$_2$O at 300° C. and 400° C. respectively in an O$_2$ flow.

Sulfated zirconia supported on silica was prepared by slurrying fumed silica gel with zirconyl nitrate and urea (1:4 molar ratio), and stirring at 90° C. for 6 hs. During this period, the slurry pH increased from ~2 to above 6, as Zr(OH)$_4$ precipitated onto silica during the homogeneous decomposition of urea. After drying at 110° C. overnight, the precipitated Zr(OH)$_4$/SiO$_2$ was slurried with 1N H$_2$SO$_4$, dried, and calcined at 600° C.

For metallocene impregnation on prepared supports, pentane was condensed onto well-mixed measured quantities of the zirconocene complex and support in a two-sided fritted reaction vessel interfaced to the high-vacuum line. The resulting slurry was next stirred for 1 h and filtered. The impregnated support was collected on the frit, washed three times with pentane, and finally dried in vacuo.

Physical and Analytical Measurements. The following instruments were used: $^1$H, $^{13}$C NMR (Varian Gemini 300), $^{13}$C CPMAS solid-state NMR(Varian VXR300), BET/pore size distribution (Omnisorb 360), thermogravimetric analysis (TA SDT 2960) XRD (Rigaku D/MAX II), ICP (Thermo Jarrell Ash Atom Scan 25), GC/MSD (Hewlett-Packard 6890), and IR (Biorad FTS-60). NMR experiments on air-sensitive samples were conducted in Teflon valve-sealed sample tubes (J-Young). For $^{13}$C CPMAS solid-state NMR, air-sensitive samples were loaded into cylindrical silicon nitride rotors in the glovebox with O-ring sealed Kel-F caps. Typically, spinning rate of 6.3 KHz could be achieved with a Doty Scientific 5 mm supersonic probe by using boil-off nitrogen as the spinning gas to prevent sample exposure to air. Kinetic olefin/arene hydrogenation studies were carried out in a constant volume, pseudo-constant-pressure gas uptake apparatus equipped with a Barocel Differential Manometer to measure small pressure changes between the gas ballasts. The glass reaction vessel (ca. 10 mL in volume) was fitted with Morton-type indentations and a high-speed vortex agitator (American Scientific MT-51 vortex mixer) to ensure efficient mixing, a water jacket connected to a recirculating pump, and a Haake constant-temperature bath (25.0(1)° C.), calibrated burets for admitting reagents, and a large diameter flexible stainless steel connection to a high-vacuum line. The gas handling system was of the Hussey-Burwell-Kung type with 1000 mL gas ballasts (all thermostated at 25.0(1)° C.). In a typical experiment, the reaction vessel was dried under high-vacuum (5×10$^{-7}$ Torr) for >2 h, taken into the glovebox, and the catalyst introduced into the reaction chamber, and the substrates into the burets. The vessel was transferred outside to the vacuum line, evacuated, and filled with H$_2$ $_f$ (1 atm). Next, the thermostated water circulating system was connected and actuated. The substrate was introduced, and the valve between the ballasts was closed. Vortex mixing was then initiated and the H$_2$ pressure was recorded as a function of time.

The catalysts were synthesized through adsorption of Ziegler-type catalysts on chemically modified (sulfate-modified) zirconia as described above. In general, Ziegler-type catalysts are slurried with sulfate-modified zirconia in hydrocarbon solvents under anaerobic conditions, and thereby irreversibly adsorbed on the surface. In hydrogenation and polymerization reactions, the catalysts are stirred with neat arenes or solutions of these substrates in a slurry mode (Table 1).

TABLE 1

Olefin/Arene Hydrogenation Catalyzed by Supported Organozirconium Complexes at 25.0 (1) ° C., PH$_2$ = 1 atm

| Entry | Complex | Solidacid | Reactant | Product | $N_t{}^a h^{-1}$ |
|---|---|---|---|---|---|
| 1. | Cp$_2$Zr(CH$_3$)$_2$(1) | ZR | 1-hexene | — | ~0 |
| 2. | 1 | ZRW | 1-hexene | — | ~0 |
| 3. | 1 | ZRS300 | 1-hexene | hexane | 32[b] |
| 4. | 1 | ZRS400 | 1-hexene | hexane | 35[b] |
| 5. | 1 | ZRS740 | 1-hexene | hexane | 7[b] |
| 6. | Cp*Zr(CH$_3$)$_3$(2) | ZRS400 | 1-hexene | hexane | 2840 |
| 7. | 2 | ZRS400 | benzene | cyclohexane | 970 |
| 8. | 2 | ZRS400 | toluene | methylcyclohexane | 14 |
| 9. | 2 | ZRS400 | p-xylene | — | ~0 |
| 10. | 2 | ZRS400 | ethylene | polyethylene | 3.9 × 10$^{4c}$ |
| 11. | Zr(CH$_2$SiMe$_3$)$_4$ | ZRS400 | benzene | cyclohexane | 12 |
| 12. | [d]CGCZr(CH$_3$)$_2$ | ZRS400 | benzene | cyclohexane | <1 |
| 13. | ZrBz$_4$[d] | ZRS400 | benzene | cyclohexane | 2 |
| 14. | TiNp$_4$[e] | ZRS400 | benzene | cyclohexane | 6.7 |
| 15. | CpTi(CH$_3$)$_3$ | ZRS400 | benzene | cyclohexane | 4 |
| 16. | Cp*Ti(CH$_3$)$_3$ | ZRS400 | benzene | cyclohexane | <1 |
| 17. | TaNp$_3$(=CHCMe$_3$)[f] | ZRS400 | benzene | cyclohexane | ~2 |

TABLE 1-continued

Olefin/Arene Hydrogenation Catalyzed by Supported Organozirconium Complexes at 25.0 (1) °C., $PH_2$ = 1 atm

| Entry | Complex | Solidacid | Reactant | Product | $N_t{}^a h^{-1}$ |
|---|---|---|---|---|---|
| 18. | Cp*TaBz$_2$(=CHPh)$^e$ | ZRS400 | benzene | cyclohexane | ~2 |
| 19. | Cp*Ta(CH$_3$)$_4$ | ZRS400 | benzene | cyclohexane$^f$ | ~0 |
| 20. | Al(CH$_3$)$_3$ | ZRS400 | benzene | cyclohexane | <1 |

$^a$Turnover frequency, $N_t$ = the number of converted substrates per catalyst metal atom per hour, which were measured while the pressure drop in system was <1%.
$^b$Precise activity measurements are complicated somewhat by competing substrate isomerization yielding cis- and trans-2-hexene.
$^c$Activity = g polyethylene / one mole of Zr atom · atm ethylene.h.
$^d$CGC = Me$_2$Si(Me$_4$C$_5$)($^t$BuN)
$^e$Bz = Benzyl.
$^f$Np = Neopentyl.
$^g$Cyclohexane was detected overnight at 70° C. All H$_2$ uptake results are corrected for substrate vapor pressure.

The Ziegler-Natta catalysts envisioned for use with the subject invention include: Cp$_m$MX$_n$Y$_p$/cocatalysts, where the catalyst is typically a Ziegler-type catalyst or a constrained geometry catalyst:

wherein:

Cp denotes a cyclopentadienyl, a substituted cyclopentadienyl radical, or a fused cyclopentadienyl radical, such as an indenyl radical.

Examples of substituted Cp groups include C$_5$R*$_4$, in which R* is selected from the group consisting of hydrogen, alkyl having 1 to 20 carbon atoms, aryl having 6 to 18 carbon atoms and triorganosilyl, such as trimethylsilyl. A specific Cp group includes tetramethylcyclopentadienyl (Cp=$\eta^5$—C$_5$Me$_4$), wherein Me hereinafter denotes a methyl radical and $\eta^5$ indicates pentahapto coordination to the metal.

Further:

M is a metal of group 3, 4, 5, 6, 7, 8, 9, 10, an element of the actinide or lanthanide groups, Al, Si, Ge, Sn, Pb, As, Sb or B, and preferably Ti, Zr or Hf;

X is an inert anionic ligand such as —CR*(C ≦20);

Y is a heteroatom ligand, such as —OR—, —SR—, —NR*—, —PR*—or a neutral two electron donor ligand selected from the group consisting of —CR*, —SR*, —NR*$_2$ or —PR*$_2$;

Z is SiR*$_2$, CR*$_2$, SiR$_2$SiR*$_2$SiR*$_2$, CR*$_2$CR*$_2$, CR*= CR*, CR*$_2$SiR*$_2$, GeR*$_2$, SnR$_2$*, wherein:

R, R*, each occurrence, is independently selected from the group consisting of hydrogen, alkyl, tin, aryl, silyl, halogenated alkyl, halogenated aryl groups having up to 20 carbon or non-hydrogen atoms, and mixtures thereof, or two or more R* groups from Y, Z or both Y and Z form a fused ring system. m,n, and p are independent of one another;

p is 0 or 1 or 2;

m is 0 or 1 or 2 or 3;

n is 1 or 2 or 3 or 4;

the sum of m and n is equal to the valence of M;

d is 1 or 2;

The cocatalyst is any metal-oxide (ZrO$_2$, Al$_2$O$_3$, TiO$_2$, HfO2, Fe2O3, SiO$_2$, and SnO$_2$, etc) or T-impregnated metal-oxide the surface of which is modified thereon by a sulfate group; high surface area/large pore size metal-oxides such as silica coated with (T-impregnated) sulfate-modified metal-oxide(s). T is one or more element(s) of (a) group 1, 2, 3, 4, 5, 6, 7, 8, 9, 10, 11, 12, 13, 14, actinide, or lanthanide group.

Zirconia (ZR) and tungsten-oxide/zirconia (ZRW) were prepared by modifications of literature procedures. Sulfated zirconia (ZRSO) was prepared by thermal decomposition of Zr(SO$_4$)$_2$•4H$_2$O (Aldrich, 99.99%) at 730 °C. for 5 h in flowing dry O$_2$ (100 mL/min). These ZRSO sample substrates were then separately activated at 300, 400 and 740° C. under high vacuum ( 5×10$^{-6}$ Torr), resulting in supports designated ZRS300, ZRS400, and ZRS400, respectively.

A poisoning experiment was carried out in which a measured concentration of degassed H$_2$O in C$_6$D$_6$ (0.050 g H$_2$O/100 g C$_6$D$_6$ at 25° C.) was dropped into the reactor, and the activity was measured. Active site calculation was based on assumption that a molecule of H$_2$O reacts with one active site resulting catalytically inert site.

The complex Cp*Zr(CH$_3$)$_3$, which is more coordinatively unsaturated and less sterically hindered than Cp$_2$Zr(CH$_3$)$_2$, exhibits a dramatic enhancement in hydrogenation activity when supported on ZRS400; for example, it mediates rapid hydrogenation of alkenes (C≦30), arenes (C≦30) such as benzene or toluene at 25° C., 1 atm H$_2$ and polymers with unsaturated substituents pendant on the polymer backbone, as well as unsaturated polymers. Rates are zero-order in the arene up to ~20% conversion and are critically affected by the arene substitution pattern (entries 7–9), in contrast to more conventional catalysts. This trend is also observed in a series of Ti catalyst activities (entries 14–16). The above substrate substituent effects suggest that the molecular surface active centers are sterically hindered. Ligand character, a possibly electronic feature, also plays a major role in hydrogenation activity (entries 6,11–12 and 16–18) as well as metal character. The benzene hydrogenation activity of Cp*Zr(CH$_3$)$_3$/ZRS400 at 25.0(1)° C., 1 atm H$_2$ rivals or exceeds that of the most active arene hydrogenation catalysts. From poisoning experiments with degassed water, ~ 65% of Cp*Zr(CH$_3$)$_3$/ZRS400 sites are determined to be of catalytic importance in benzene hydrogenation, vs ~4% for Cp*$_2$Th(CH$_3$)$_2$/dehydroxylated alumina. Cp$_2$Zr(CH$_3$)$_2$/ZRS400 and Cp*Zr(CH$_3$)$_3$/ZRS400 also catalyze homopolymerization in α-olefins (C ≦10), such as ethylene with preliminary activity measurements indicating 1.5×10$^3$ and 4.0×10$^4$ g PE/mol Zr.h.atm C$_2$H$_4$, respectively.

Insight into the metallocene chernisorption process on sulfated zirconia is provided by $^{13}$C CPMAS NMR spectroscopy with known anaerobic sampling and assignment techniques and using Cp*$_2$Th($^{13}$CH$_3$)$_2$ and Cp$_2$Zr($^{13}$CH$_3$)$_2$ as model adsorbates. The $^{13}$C CPMAS NMR spectrum of Cp*$_2$Th($^{13}$CH$_3$)$_2$/ZRS400 (FIG. 1a) exhibits resonances assignable to the Cp* ligands (δ127.6, 9.3), to the labeled Th—$^{13}$CH$_3$ functionality (A; δ72.8) and to μ-oxo species Cp*$_2$Th($^{13}$CH$_3$)—O—(B; δ54.2). Interestingly, Th—$^{13}$CH$_3$=δ72.8 on ZRS400 is at significantly lower field than is associated with analogous "cation-like" species on other supports, and is suggestive of a more electron-deficient species. Two small additional resonances are observed at δ 32.6 and −0.2. Although they could not be rigorously assigned, the chemical shifts can be correlated with tansferred methide groups i.e, S$_{surface}$-$^{13}$CH$_3$ (c.f., HOS(O)$_2$ CH$_3$, δ 39.4) and Zr$_{surface}$-$^{13}$CH$_3$, respectively. However, both signals are very weak in intensity compared to the Th—CH$_3$ resonance ( ca. 5%). Therefore, methide transfer to the surface is not as important on sulfated zirconia as on dehydroxylated alumina, which exhibits an intense of Al$_{surface}$-$^{13}$CH$_3$resonance (δ−12), almost equal in intensity to the Th—$^{13}$CH$_3$$^+$ signal.

FIG. 1 (b) presents the $^{13}$C CPMAS NMR spectrum of Cp$_2$Zr($^{13}$CH$_3$)$_2$/ZRS400. Only two resonances are detected at δ 113.8 (Cp ligand) and δ 36 (cationic Zr—$^{13}$CH$_3$) with a small shoulder at about δ 20 assignable to the μ-oxo species, and a transferred methide group resonance is not observable. Similar observations are made for Cp*Zr(CH$_3$)$_3$ (2) /ZRS400, an active arene hydrogenation catalyst (FIG. 1a)). Resonances at δ 123.8 and 51.4 are assigned to the Cp* ligand and cationic Zr—$^{13}$CH$_3$ group, respectively. The latter resonance diminishes

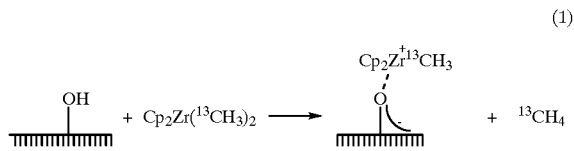

(1)

greatly upon hydrogenation due to hydrogenolysis of the Zr—$^{13}$CH$_3$ bond (FIG. 2b). These spectroscopic results argue that sulfated zirconia Brønsted acid sites generate cationic adsorbate species via metal-carbon bond protonolysis (eq 1). This proposed pathway is supported by the following observations: (1) the correlation of Cp$_2$Zr(CH$_3$)$_2$ /ZRSx catalytic activities (entries 3–5 in Table 1) with the density of support Brønsted acid sites, (2) after impregnation of Cp2Zr(CH$_3$)2 on ZRS400, the $v_{OH}$, transition in the infrared (3650 cm$^{-1}$) disappears, accompanied by a shift of $v_{S=O}$ from 1395 cm$^{-1}$ to 1360 cm$^{-1}$, and (3) methane is detected in the $^1$H NMR spectrum (δ 0.15) of a Cp$_2$Zr(CH$_3$) $_2$+ZRS400 mixture in C$_6$D$_6$. The observations that homogeneous (X$^-$) and heterogeneous oxo counteranions such as CF$_3$SO$_3^-$(H$_O$=−14.1) and ZRW (H$_O$≦−14.5) afford catalytically inert species suggests that a sulfated zirconia support contains Brønsted acid sites stronger than H$_O$=−14 and/or having charge-delocalized, weakly coordinating conjugate base anionic sites such as shown with structure A in reaction 1.

EXAMPLE 1

Sulfated zirconia (ZRSO) was prepared by thermal decomposition of Zr(SO$_4$)$_2$•4H$_2$O in an O$_2$ flow as set forth above. Then, the ZRSO samples were activated at 300, 400, and 740° C. under high-vacuum resulting in a cocatalyst designated ZRS300, ZRS400, and ZRS740, respectively. In a two-sided fritted reaction vessel interfaced to the high-vacuum line; 10 mL of pentane was condensed onto well-mixed, measured quantities of the Cp*Zr(CH$_3$)$_3$ (38 mg, 0.148 mmol) [Cp*=η$^5$-(CH$_3$)$_5$C$_5$] and ZRS400 (1.0 g). The resulting slurry was next stirred for 1 h and filtered. The impregnated support was collected on the frit, washed three times with pentane, and finally dried in vacuo. The benzene hydrogenation rates were measured of the benzene over the prepared catalyst slurry in a constant volume, pseudo-constant-pressure H$_2$ uptake apparatus with rapid stirring at 25.0(1)° C., 1 atm H$_2$. Cyclohexane is the exclusive product as confirmed by GC/MSD (N$_t$=970 h$^{-1}$).

EXAMPLE 2

ZRS400 was prepared as in Example 1 in a two-sided fritted reaction vessel interfaced to the high-vacuum line; 10 mL of pentane was condensed onto well-mixed measured quantities of the Cp*Zr(CH$_3$)$_3$ (39 mg, 0.148 mmol) [Cp*= η$^5$-(CH$_3$)$_5$C$_5$] and ZRS400 (1.0 g). The resulting slurry was next stirred for 1 h and filtered. The impregnated support was collected on the frit, washed three times with pentane, and finally dried in vacuo. The toluene hydrogenation rate was measured with rapid mixing of toluene over the supported catalyst slurry in a constant volume, pseudo-constant-pressure H$_2$ uptake apparatus at 25.0(1)° C., 1 atm H$_2$. Methylcyclohexane was the exclusive product as confirmed by GC/MSD (N$_t$=14 h$^{-1}$).

EXAMPLE 3

ZRS400 was prepared as in Example 1 in a two-sided flitted reaction vessel interfaced to the high-vacuum line; 10 mL of pentane was condensed onto well-mixed measured quantities of the Cp*Zr(CH$_3$)$_3$ (39 mg, 0.148 mmol) [Cp*= η$^5$-(CH$_3$)$_5$C$_5$] and ZRS400 (1.0 g). The resulting slurry was next stirred for 1 h and filtered. The impregnated support was collected on the frit, washed three times with pentane, and finally dried in vacuo. Ethylene homopolymerization was performed with rapid mixing of the ethylene over the prepared catalyst in 20 mL of toluene. The polyethylene product was dried overnight under high-vacuum and weighed (activity=3.9×10$^4$ g/mol of Zr.h.atm of ethylene).

EXAMPLE 4

ZRS400 was prepared as in Example 1 in a two-sided fritted reaction vessel interfaced to the high-vacuum line; 10 mL of pentane was condensed onto well-mixed measured quantities of the Zr(CH$_2$SiMe$_3$)$_4$ (21.6 mg, 0.049 mmol) and ZRS400 (1.0 g). The resulting slurry was next stirred for 1 h and filtered. The impregnated support was collected on the frit, washed three times with pentane, and finally dried in vacuo. The benzene hydrogenation rate was measured with rapid mixing of the benzene over the prepared catalyst in a constant volume, pseudo-constant-pressure H$_2$ uptake apparatus at 25.0(1)° C., 1 atm H$_2$. Cyclohexane was the exclusive product as confirmed by GC/MSD (N$_t$=12 h$^{-1}$).

EXAMPLE 5

ZRS400 was prepared as in Example 1 in a two-sided fritted reaction vessel interfaced to the high-vacuum line; 10 mL of pentane was condensed onto well-mixed measured quantities of CGCZr(CH$_3$)$_2$ (18.2 mg, 0.049 inmol) [CGC= Me$_2$Si(Me$_4$Cs)($^t$BuN)] and ZRS400 (1.0 g). The resulting slurry was next stirred for 1 h and filtered. The impregnated support was collected on the frit, washed three times with pentane, and finally dried in vacuo. The benzene hydrogenation rate was measured with rapid mixing of benzene over the prepared catalyst slurry in a constant volume, pseudo-constant-pressure $H_2$ uptake apparatus at 25.0(1)° C., 1 atm $H_2$. Cyclohexane was the exclusive product as confirmed by GC/MSD ( $N_t \leq 1$ $h^{-1}$).).

EXAMPLE 6

ZRS400 was prepared as in Example 1 in a two-sided fritted reaction vessel interfaced to the high-vacuum line; 10 mL of pentane was condensed onto well-mixed measured quantities of the $ZrBz_4$ (22.3 mg, 0.049 nunol) [$Bz=CH_2Ph$] and ZRS400 (1.0 g). The resulting slurry was next stiffed for 1 h and filtered. The impregnated support was collected on the frit, washed three times with pentane, and finally dried in vacuo. The benzene hydrogenation rate was measured with rapid mixing of benzene over the prepared catalyst slurry in a constant volume, pseudo-constant-pressure $H_2$ uptake apparatus at 25.0(1)° C., 1 atm $H_2$. Cyclohexane was the exclusive product as confirmed by GC/MSD ($N_t=2$ $h^{-1}$).

EXAMPLE 7

ZRS400 was prepared as in Example 1 in a two-sided fritted reaction vessel interfaced to the high-vacuum line; 10 mL of pentane was condensed onto well-mixed measured quantities of $TiNp_4$ (16.3 mg, 0.049 mmol) [$Np=CH_2CMe_3$] and ZRS400 (1.0 g). The resulting slurry was next stirred for 1 h at −78° C. and cold-filtered. The impregnated support was collected on the frit, washed three times with pentane, and finally dried in vacuo. The benzene hydrogenation rate was measured with rapid mixing of the benzene over the prepared catalyst slurry in a constant volume, pseudo-constant-pressure $H_2$ uptake apparatus at 25.0(1)° C., 1 atm $H_2$. Cyclohexane was the exclusive product as confirmed by GC/MSD ($N_t=6.7$ $h^{-1}$).

EXAMPLE 8

ZRS400 was prepared as in Example 1 in a two-sided fritted reaction vessel interfaced to the high-vacuum line; 10 mL of pentane was condensed onto well-mixed measured quantities of the $CpTi(CH_3)_3$ (7.7 mg, 0.049 mmol) [$Cp=\eta^5-C_5H_5$] and ZRS400 (1.0 g). The resulting slurry was next stirred for 1 h at −78° C. and cold-filtered. The impregnated support was collected on the frit, washed three times with pentane, and finally dried in vacuo. The benzene hydrogenation rate was measured with rapid mixing of the benzene over the prepared catalyst slurry in a constant volume, pseudo-constant-pressure $H_2$ uptake apparatus at 25.0(1)° C., 1 atm $H_2$. Methylcyclohexane was the exclusive product as confirmed by GC/MSD ($N_t=4h^{-1}$).

EXAMPLE 9

ZRS400 was prepared as in Example 1 in a two-sided fritted reaction vessel interfaced to the high-vacuum line; 10 mL of pentane was condensed onto well-mixed measured quantities of the $Cp*Ti(CH_3)_3$ (11.4 mg, 0.049 mmol) [$Cp*=\eta^5-(CH_3)_5C_5$] and ZRS400 (1.0 g). The resulting slurry was next stirred for 1 h at −78° C. and cold-filtered. The impregnated support was collected on the frit, washed three times with pentane, and finally dried in vacuo. The benzene hydrogenation rate was measured with rapid mixing of the benzene over the prepared catalyst slurry in a constant volume, pseudo-constant-pressure $H_2$ uptake apparatus at 25.0(1)° C., 1 atm $H_2$. Methylcyclohexane was the exclusive product as confirmed by GC/MSD ($N_t \leq 1$ $h^{-1}$).

EXAMPLE 10

ZRS400 was prepared as in Example 1 in a two-sided fritted reaction vessel interfaced to the high-vacuum line; 10 mL of pentane was condensed onto well-mixed measured quantities of the $TaNp_3(=CHCMe_3)$ ( 22.8 mg, 0.049 mmol) [$Np=CH_2CMe_3$] and ZRS400 (1.0 g). The resulting slurry was next stirred for 1 h at −78° C. and cold-filtered. The impregnated support was collected on the frit, washed three times with pentane, and finally dried in vacuo. The benzene hydrogenation rate was measured with rapid mixing of the benzene over the prepared catalyst slurry in a constant volume, pseudo-constant-pressure $H_2$ uptake apparatus at 25.0(1)° C., 1 atm $H_2$. Cyclohexane was the exclusive product as confirmed by GC/MSD ($N_t=\sim 2$ $h^{-1}$).

EXAMPLE 11

ZRS400 was prepared as in Example 1 in a two-sided fritted reaction vessel interfaced to the high-vacuum line; 10 mL of pentane was condensed onto well-mixed measured quantities of the $Cp*TaBz_2$ (28.8 mg, 0.049 mmol) [$Cp*=\eta^5-(CH_3)_5C_5$; $Bz=CH_2Ph$] and ZRS400 (1.0 g). The resulting slurry was next stirred for 1 h and filtered. The impregnated support was collected on the frit, washed three times with pentane, and finally dried in vacuo. The benzene hydrogenation rate was measured with rapid mixing of the benzene over the prepared catalyst slurry in a constant volume, pseudo-constant-pressure $H_2$ uptake apparatus at 25.0(1)° C., 1 atm $H_2$. Cyclohexane was the exclusive product as confirmed by GC/MSD ( $N_t=2$ $h^{-1}$).

EXAMPLE 12

ZRS400 was prepared as in Example 1 in a two-sided flitted reaction vessel interfaced to the high-vacuum line; 10 mL of pentane was condensed onto measured quantities of the $Al(CH_3)_3$ (3.6 mg, 0.049 mmol) and the resulting solution was yielded to react with ZRS400 (1.0 g) at −78° C. The resulting slurry was next stirred for 1 h at room temperature and filtered. The impregnated support was collected on the frit, washed three times with pentane, and finally dried in vacuo. The benzene hydrogenation rate was measured with rapid mixing of the benzene over the prepared catalyst in a constant volume, pseudo-constant-pressure $H_2$ uptake apparatus at 25.0(1)° C., 1 atm $H_2$. Cyclohexane was the exclusive product as confirmed by GC/MSD($N_t \leq 1$ $h^{-1}$).

By the subject invention, olefins (C $\leq$30) such as ethylene, propylene and butadiene, arenes (C $\leq$30), polymers with pendant arene and alkene substituents, and unsaturated or partially saturated polymers may be hydrogenated. For example, benzene may be hydrogenated to cyclohexane to provide the feedstock for making adipic acid, a major intermediate in production of nylon. The catalysts of the subject invention are a good substitute for those catalysts which require harsh conditions ( typically, temperature >100° C., $H_2$ pressure>5 atm) to hydrogenate benzene to cyclohexane. Also, the present invention may be applied to hydrogenating olefins (C$\leq$30) and arenes (C $\leq$30) in gasoline to hydrogenated products. The olefin polymerization catalysts by the subject invention can be applied to produce microstructually unusual polymers from α-olefins, and particularly from two different kinds of catalytic centers—Brønsted acidic (cationic olefin oligomerization) and Ziegler-Natta catalytic sites (olefin polymerization and olefin/arene hydrogenation).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents.

What is claimed is:

1. A compound for use in hydrogenation and polymerization reactions comprising $R_xMR'_y$, where R, $R^1$ is a cyclopentadienyl ligand, an alkyl (C 20), an alkenyl (C 20), or an aryl group (C 20)

M is Zr, Ti, Hf, V, Nb, Ta, Lanthanide, Al, Si, Ge, Sn, Pb, As, Sb, or B;

X is 0 to 3

Y is 0 to 3 said compound being adsorbed on a substrate selected from the group consisting of sulfate modified zirconia; zirconia/tungsten oxide; acidic sulfated zirconia, sulfated zirconia on silicon, and sulfated metal oxides based on Ti or Hf.

* * * * *